US005300921A

United States Patent [19]
Hoch et al.

[11] Patent Number: 5,300,921
[45] Date of Patent: Apr. 5, 1994

[54] ATHLETIC TRAINING SYSTEM

[75] Inventors: David J. Hoch, Cambridge; Alexander R. Thomas, Groveland, both of Mass.

[73] Assignee: Rhys Resources Ins., Groveland, Mass.

[21] Appl. No.: 976,175

[22] Filed: Nov. 13, 1992

[51] Int. Cl.$^5$ ............................................. G08B 21/00
[52] U.S. Cl. ........................... 340/573; 273/29 A; 273/DIG. 17; 340/689; 434/247
[58] Field of Search ............. 340/573, 689; 273/29 A, 273/460, DIG. 17; 434/247

[56] References Cited

U.S. PATENT DOCUMENTS

| | | | |
|---|---|---|---|
| 2,754,497 | 7/1956 | Wolpert | 340/689 |
| 3,362,023 | 1/1968 | McMahon | 340/573 |
| 4,527,982 | 7/1985 | Salzman et al. | 273/29 A |
| 4,665,388 | 5/1987 | Ivie et al. | 340/573 |
| 5,005,835 | 4/1991 | Huffman | 273/DIG. 17 |
| 5,158,089 | 10/1992 | Swezey et al. | 340/573 |

*Primary Examiner*—Glen R. Swann, III
*Attorney, Agent, or Firm*—Dirk Brinkman

[57] ABSTRACT

A position processor can be mounted on the head of an athlete by means of, for example, a head band. The position processor includes a sensor in the form of a twelve position mercury switch for sensing the direction and angle of tilt of the head. The ON/OFF states of the switches of the sensor are sampled by a multiplexer under the control of a microprocesor. The multiplexer presents the ON/OFF states to the microprocessor for further procesing. Software of the microprocessor processes the sensed ON/OFF states through filtering and hysterisis algorithms and conveys the processed states as positional information to the athlete as a pattern of lights and tones. Proper and improper head positions are indicated for a plurality of directions of tilt. The system uses software filtering to provide hysterisis in order to eliminate rapid changes of state of the switches of the sensor due to sporadic movement caused by the motion of the athelete. The training system is user controllable by means of rotary switches to adjust, among other things, the level of sensitivity of the system.

9 Claims, 9 Drawing Sheets

ATHLETIC TRAINING SYSTEM

FIELD OF THE INVENTION

This invention relates generally to systems for monitoring body positions, and more particularly, to a training system for tennis players.

BACKGROUND OF THE INVENTION

It is a problem to reliably and acurately monitor the position of a human body during various activities. For example, is important for athletes to monitor and maintain proper body position while performing or training for athletic events. In the game of tennis, it is particularly important for the tennis player to keep his or her head in what is known as a "head-up" position, not only when approaching the ball, but also while stroking the ball with the racquet. Professional tennis players recognize that maintaining a proper head-up position is a key factor in perfecting one's proficiency in the game. It is a problem to provide the tennis player or tennis coach with visual or audible cues to indicate that the player's head is in the proper head-up position.

Numerous systems are known in the prior art for indicating a player's head position during sports activities. However, the known systems generally require substantial set-up in order to operate properly. Furthermore, the known systems generally are best suited for sports activities where the player's body is in a relative static position, and head movement is relatively infrequent, and the head position is only critical for a short period of time.

For example, a number training systems are known for golf players which give an indication if the golf player lifts his head head prematurely during a golf swing. That is, the device mounted on the golf player's head simply gives an alarm when it senses any movement of the head.

The game of tennis, unlike golf, requires that the player moves rapidly on the court, frequently shifting body position, with sudden stops and starts, while responding to the celeritous movement of the tennis ball. As the player moves, the head is likely to bob up, down, and sideways with relative frequency, and thus, known training systems would too often give erroneous positional information, making them difficult and annoying to use.

Therefore, there is a need for a training system which can reliably monitor and indicate head positions while the tennis player moves on the court. Furthermore, it is desirable that such a system be simple to operate while giving the player and the coach accurate positional information.

SUMMARY OF THE INVENTION

An athletic training system, that is hardware and software, is provided for helping an athlete maintain a proper body position. More specifically, the training system can be used to monitor the head position of an athlete, such as a tennis player, while playing tennis. Head positions being the direction of tilt, from the vertical axis of the head. A substantial vertical alignment of the head with the rest of the body, known as a head-up position, being deemed a proper head position for playing tennis, and a significant deviation from vertical, in any direction, being deemed an improper head position. The system includes a position processor which can be mounted on the head of an athlete by means of, for example, a head band.

The position processor includes a sensor in the form of a twelve position mercury switch. The mercury switch includes a mercury droplet which contacts the pins of the switch if the sensor is displaced or tilted from an essentially horizontal position in any direction. The number of pins concurrently contacted by the mercury droplet varies with the relative severity or angle of tilt of the sensor. The ON/OFF states of the switches of the sensor are sampled by a multiplexer under the control of a microprocessor. The multiplexer presents the ON/OFF states to the microprocessor for further processing. Software of the microprocessor processes the sensed ON/OFF states and conveys the processed states as positional information to the athlete by using a visual and audio unit. The visual unit includes a plurality of indicator lights for displaying positional information. The audio unit includes a tone generator, or optionally, a digital voice synthesizer to convey positional information to the user as readily distinguishable tones. Proper and improper head positions are indicated for a plurality of directions of tilt. The system uses software filtering and hysterisis algorithms in order to eliminate rapid changes of state of the switches of the sensor due to sporadic movement caused by the motion of the athlete. The system indicates whether the head is improperly tilted in direction quadrants, e.g., forward, backward, left, or right, or whether the head is properly positioned in a head-up position with the axis of the head being aligned substantially vertical.

In addition, the microprocessor is provided with an angle/sensitivity selector and a quadrant selector both implemented as a hex rotary switches which can be manipulated by the user. The angle/sensitivy selector allows the user, depending on his or her ability and quickness of movement, to select the relative angle of tilt which should be indicated, and the sample rate. The sample rate determining the relative sensitivity of the traning system. The quadrant selector is used to selectively surpress the conveyance improper head positions for predetermined directions. The training system also includes a power time-out feature, to conserve power, if no movement is detected in a predetermined time period.

These and other features and advantages of the present invention will become apparent from a reading of the detailed description in conjunction with the attached drawings in which like reference numerals refer to like elements in the several views.

DETAILED DESCRIPTION OF THE PREFERRED EMBODIMENT

Figure 1:
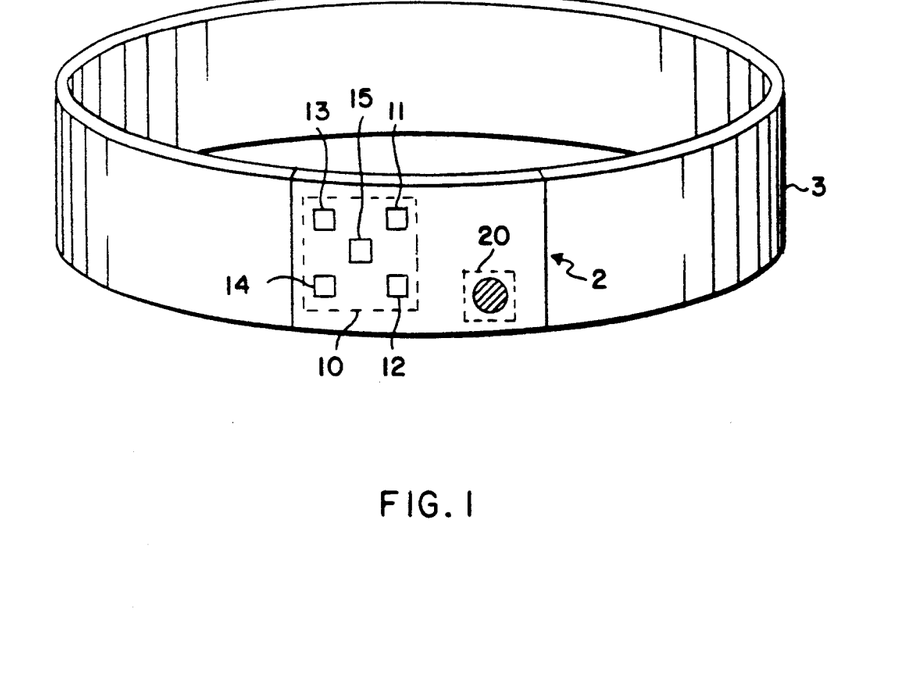
FIG. 1 is a perspective side view of the tennis training system according to the present invention.

FIG. 1 is a side view of a tennis training system embodying the present invention as it would be worn on the head of a tennis player. The system is used to teach the tennis player to maintain a proper "head-up" position while playing tennis.

The system includes a position processor 2, mounted on a head band 3. It should be apparent to one skilled in the art, that other means can also be used to mount the position processor 2 on a tennis player's head. For example, the position processor 2 can be fixed to a cap worn by the tennis player.

As an introduction, and to facilitate the understanding of the detailed description, the gross characteristics and operation of the training system during tennis playing will first be described. This introduction will be followed by a detailed description of the various elements of the system and their operations.

During the playing of tennis, it is important that the player's head is maintained in an head-up position. That is, the axis of the head is maintained substantially vertical. When the head is so positioned, the player can easily track the rapidly moving ball, and balance is also improved. If the head is not positioned in a proper head-up position the player's performance is generally deteriorated.

Figure 2:
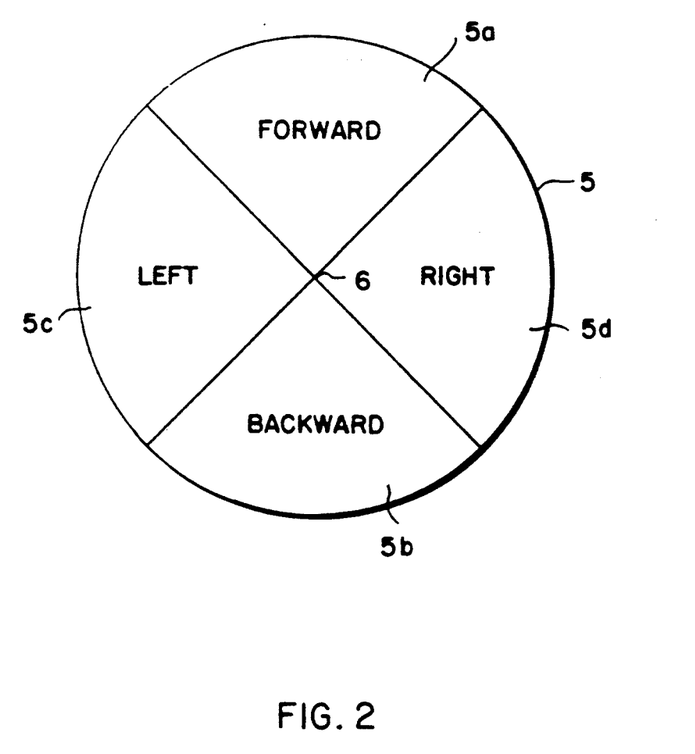
FIG. 2 is a top cross sectional view of head positions of the user of the system of FIG. 1.

FIG. 2, is a schematic cross section, of the head 5, as seen from above the tennis player. For the purpose of the present invention, improper positions of the head are classified into four quadrants, each approximately ninety degrees in extent, for example, the quadrants, 5a, 5b, 5c, and 5d, generally labeled "FORWARD," "BACKWARD," "LEFT," and "RIGHT." FORWARD is the position when the head 5 of the tennis player is tilted generally forward, e.g., face down, or towards the ground. The other positions likewise refer to the head 5 being tilted either to the back (BACKWARD), e.g., face upwards to the sky, LEFT (left ear lower than left ear, or RIGHT (right ear lower than left ear). As previously stated the head 5 is properly positioned when the axis of the head, indicated by reference numeral 6, is maintained substantially vertical, that is, neither FORWARD, BACKWARD, LEFT, nor RIGHT.

Figure 7:
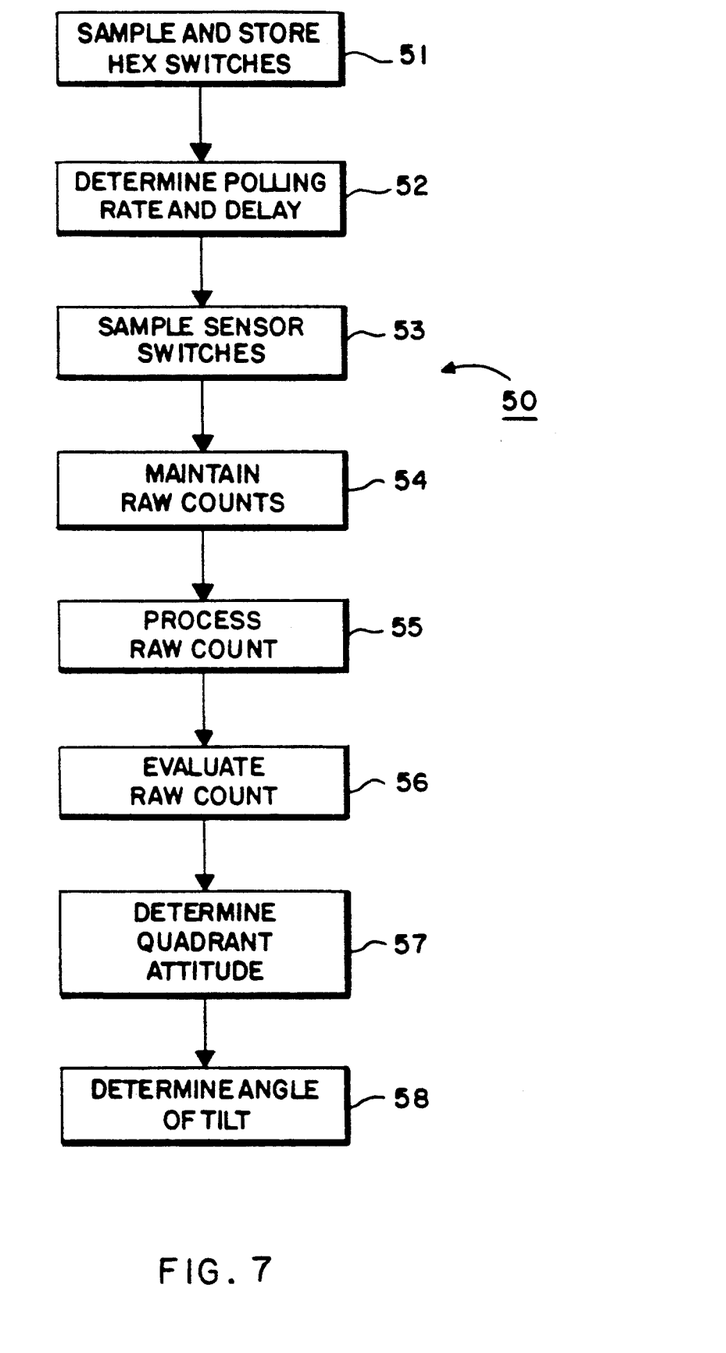
FIG. 7 is a block diagram of a polling procedure.
Figure 9:
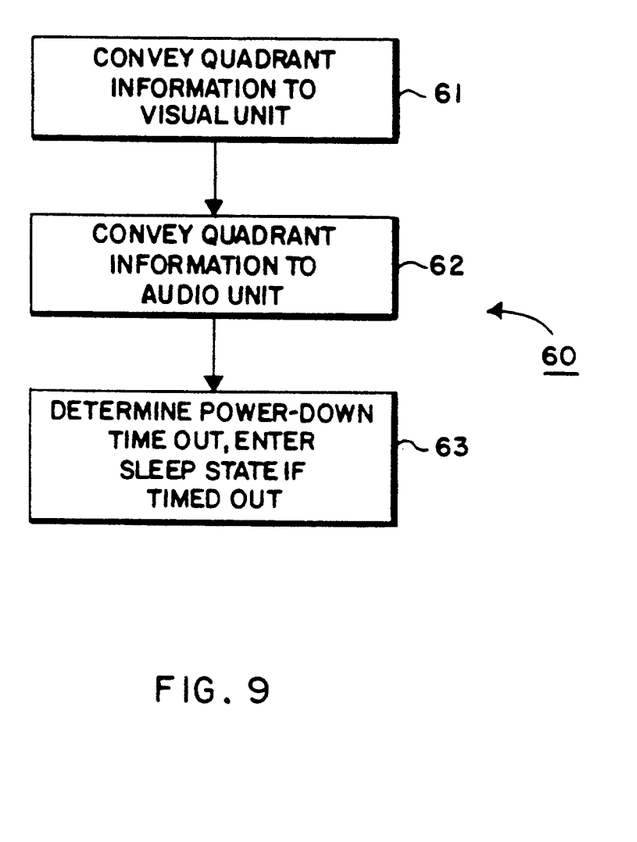
FIG. 9 is a block diagram of an interrupt procedure.

Now again with reference to FIG. 1, the positions of the head are conveyed to the tennis player by a visual unit and an audio unit, generally indicated by dashed lines 10 and 20, respectively. The visual and audio units, 10 and 20 are used, as will be described in greater detail herein, to convey positional information of the head to the tennis player, or to a person who is teaching the tennis player, such as a professional tennis coach. The positional information is sensed by a attitude and angle sensor 100 (FIG. 5) and processed by an electronic circuit (FIG. 4), including a microprocessor 40 running software (FIG. 7 and 9).

The visual unit 10 includes five light emitting diodes (LEDs), 11-15. LEDs 11-14 emit red light, and LED 15 emits green light. Depending on the position of the tennis player's head, the light patterns displayed are as follows: if the head is FORWARD, LEDs 11 and 12 are turned on; if the head is tilted BACKWARD, LEDs 13 and 14 are turned on; if the head is tilted LEFT, LEDs 11 and 13 are turned on; and if the head is tilted RIGHT, LEDs 12 and 14 are turned on. Otherwise, if the head is in the proper head-up position, or not tilted in any direction, the green LED 15 is on. It should be apparent to one skilled in the art that other light patterns and colors may also be used.

In conjunction with the positional information conveyed by the visual unit 10, the audio unit 20 generates audible tones: a 3000 Hz tone when the head is tilted FORWARD; a 1500 Hz tone when the head is tilted BACKWARD; a pulsed 3000 Hz tone if the head is tilted LEFT; and a pulsed 1500 Hz tone when the head is tilted RIGHT. No tone is generated when the head is substantially vertical. In an alternative embodiment, the audio unit 20 by means of a digital voice synthesizer emits the words "FORWARD", "BACKWARDS", "LEFT", and "RIGHT" to indicate the positions of the head.

Figure 3:
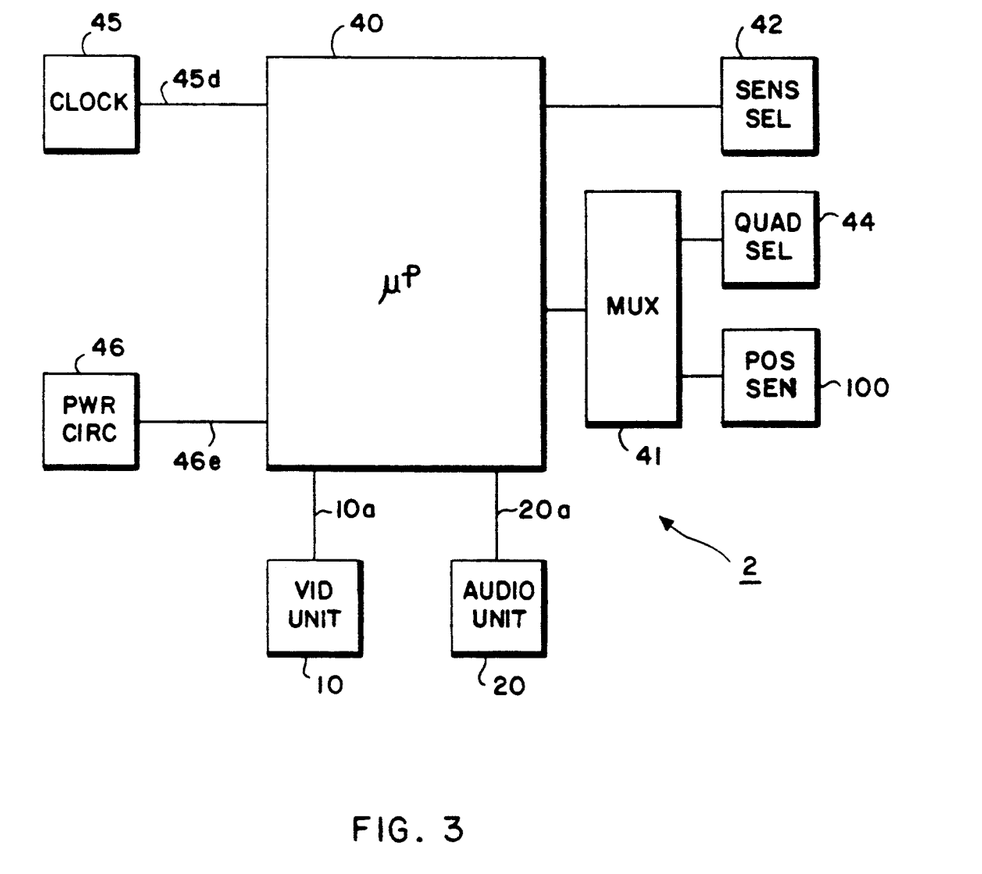
FIG. 3 is a top level block diagram of the system of FIG. 1.

Now first with reference to FIG. 3 the functional circuit blocks of the position processor 2 are described. The position processor 2 includes a microprocessor 40, a position sensor 100, a multiplexer (MUX) 41, an angle/sensitivity selector (ASSEL) 42, a quadrant selector (QSEL) 44, a clocking circuit 45, and a power on/off circuit 46. Also shown in FIG. 4 are the visual unit 10 and the audio unit 20.

Figure 4:
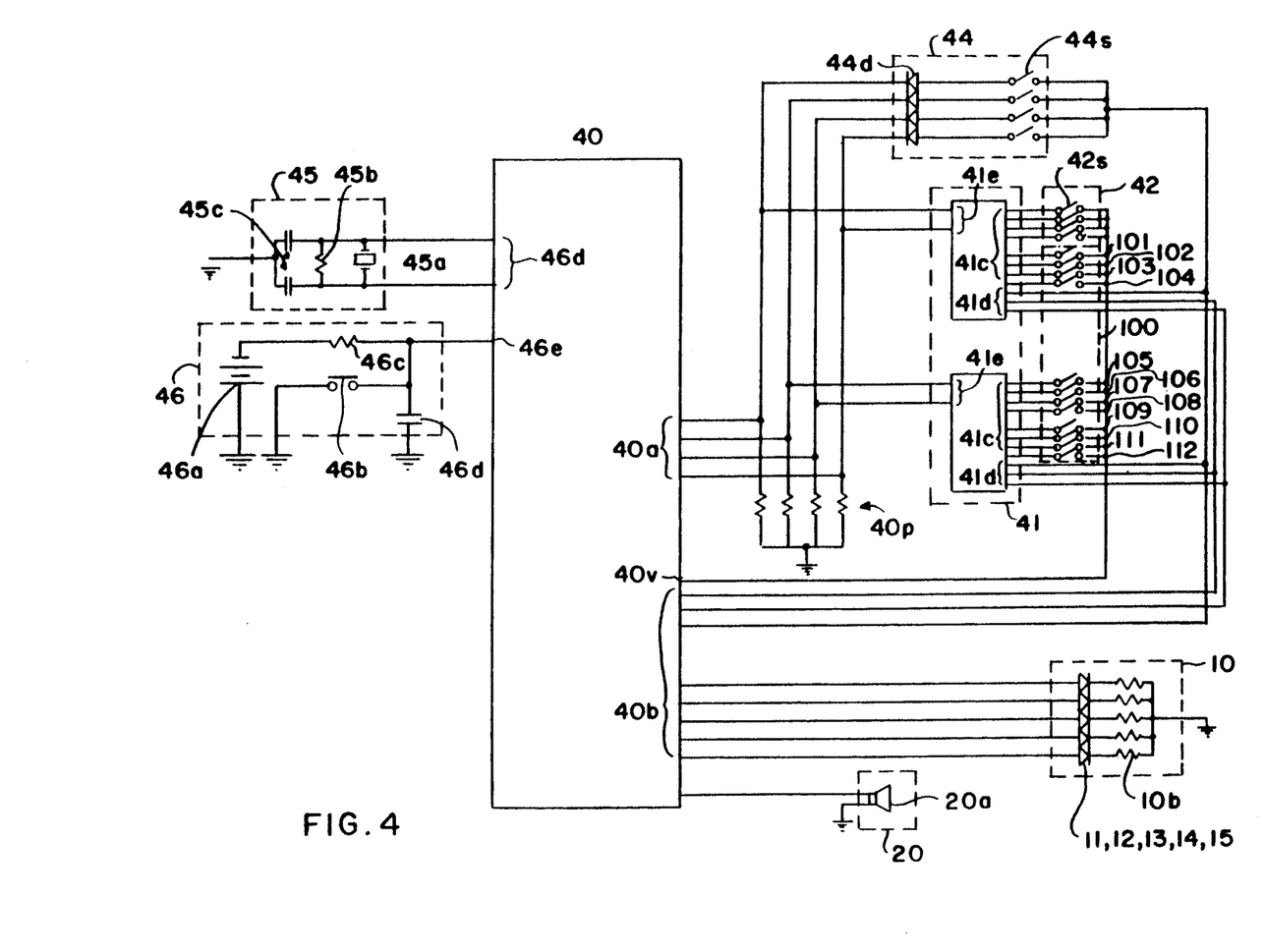
FIG. 4 is a detailed schematic diagram of the circuits of the system of FIG. 1.

Now also with reference to FIG. 4, the position processor 2 is described in greater detail. In the preferred embodiment, the microprocessor 40 is a Motorola MC68HC705J2. The microprocessor 40 includes 2K bytes of memory for storing data and instructions, 64 general purpose registers, and input ports 40a and output ports 40b, for receiving and sending data, respectively.

Figure 6A:
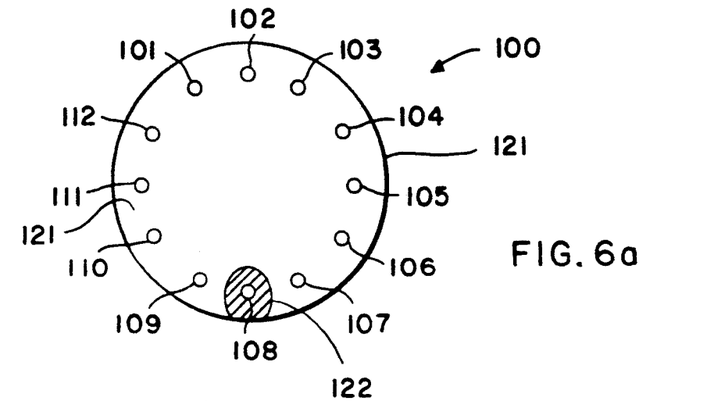
FIG. 6a, 6b, and 6c show the sensor of FIG. 5 at various angles of tilt.
Figure 6B:
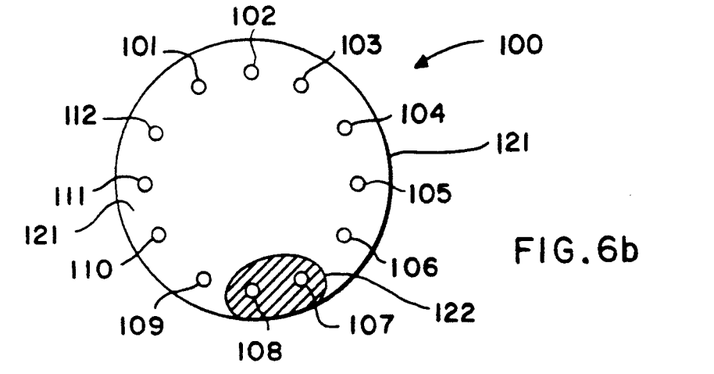
Figure 6C:
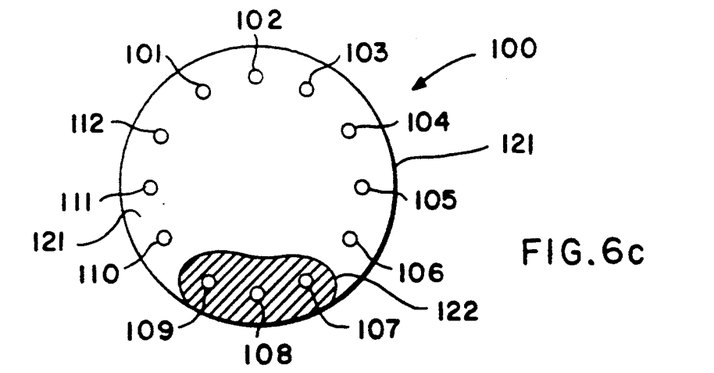

The position sensor 100, as will be described in further detail with respect to FIG. 6, is in the form of a conventional twelve position mercury switch, that is the position sensor 100 includes 12 sensing ON/OFF switches 101-112. The sensor 100 is mounted in the position processor 2, so that when the processor 2 is positioned on the head of the tennis player, the sensor is essentially level, and none of the ON/OFF switches of the mercury switch are in an ON position.

One side of each of the switches 101-112 is connected to the MUX 41 via sense lines 41c, the other side is connected to the microprocesor 40 via sensor enable line 40v. The switches 101-112 of the sensor 100 are selected by the microprocesor 40 via the MUX 41. In the preferred embodiment, the MUX 41 is implemented with two National CD4052 multiplexer circuits 41a and 41b. Each of the circuits 41a and 41b includes eight sense lines 41c which are controlled from some of the output ports 40b of the microprocesor 40 by the select lines 41d to present switch information (ON/OFF states) to the input ports 40a of the microprocessor 40 on data lines 41e, each of the data lines 40e also connected to ground via a 10K ohm resistor 40p.

Twelve of the sixteen (2×8) sense lines 41c are used for the switches 101-112 of the sensor 100, the remaining four sense lines 41c are used for the ASSEL 42. The QSEL 44 is connected directly to the input ports 40a of the microprocessor 40 via data lines 41e.

The ASSEL 42 and QSEL 44 are implemented by using two conventional sixteen position (hex) rotary switches 42s and 44s, respectively. Suitable switches 42s and 44s are, for example, MORS ASC 65503 switches. The ASSEL 42 is implemented by using the switch 42s, and the QSEL 44 is implemented by using switch 44s. The sixteen switch positions (0-15) are indicated by various combinations of four ON/OFF switches, that is $2^4$ or 16 different combinations of the switch 42s and 44s are possible. For example, position "0" is indicated as OFF, OFF, OFF, OFF, position "1" as OFF, OFF, OFF, ON, and so forth.

The QSEL 44 also includes four diodes 44d configured in the circuit to allow independent isolation of switches 44s when read by the microprocessor 40.

The clocking circuit 45 includes a 4 MHz ceramic resonator 45a. The clocking circuit 45 also includes a 4.7M ohm resistor 45b and two 25 of capacitors 45c configured conventionally. The output of the clocking circuit 45, that is, a 4 MHz clock signal, is connected to the microprocessor 40 via lines 46d.

The power on-off circuit 46 includes a 4.5 V battery 46a and a push-button power ON/OFF switch 46b. The resistor 46c and the capacitor 46d of the power on/off circuit 46 are, respectively, 10K ohm and 0.1 micro farads. The power on/off circuit 46 is connected to the microprocessor 40 via line 46e.

The visual unit 10 includes the LEDs 11-15, one side of each LED 11-15 connected to the output ports 40b of the microprocessor 40, and the other side of each of the LEDs 11-15 connected to ground via a 150 ohm resistors 10b.

The audio unit 20 is in the form of a piezo electric transducer 20a. One side of the transducer 20a is connected to one of the output ports 40b of the microprocessor 40, and the other side of the transducer 20a is connected to ground. In an alternative embodiment, the audio unit 20 is in the form of a digital voice synthesizer, which generates the words "forward," "backward," "left," and "right" to indicate the position of the head.

The electrical operation of the position processor 2 is first described. This description will be followed by a description of the software, in the form of instructions and data, permanently stored in the memory of the microprocessor 40, which is used to control and process the electrical signals of the position processor 2.

The position processor 2 is activated by the user, for example the tennis player pushing the power ON/OFF switch 46b of the power on/off circuit 46 to an "ON" position. This action causes the microprocessor 40 to exit a "sleep" mode and enter an "active" mode to power the various circuits 41-46, 10, and 20 of the position processor 2. The clock circuit 45 generates the necessary clock signal to operate the microprocessor 40 via lines 46d.

The supply of power to the microprocesor causes a hardware interrupt which activates the execution of software. The software of the microprocessor 40 is used to periodically sample the ON/OFF states of the position sensor switches 101-112, and the ON/OFF states of the switches 42s and 44s of the ASSEL 42 and the QSEL 44 by appropriately controlling the select lines 41d of the MUX 41. The ON/OFF states of the position sensor 100 switches 101-112, and the ASSEL 42 and the QSEL 44 switches 42s-44s are presented on data lines 41e to the input ports 40a of the microprocessor 40. The switch positions (ON or OFF) are processed by the software, and appropriate signals are supplied via the output ports 40b to the visual unit 10 and the audio unit 20 to give positional information to the user. The purpose and operation of the ASEL 42 and the QSEL 44 will be described with reference to FIGS. 7 and 8.

Figure 5:
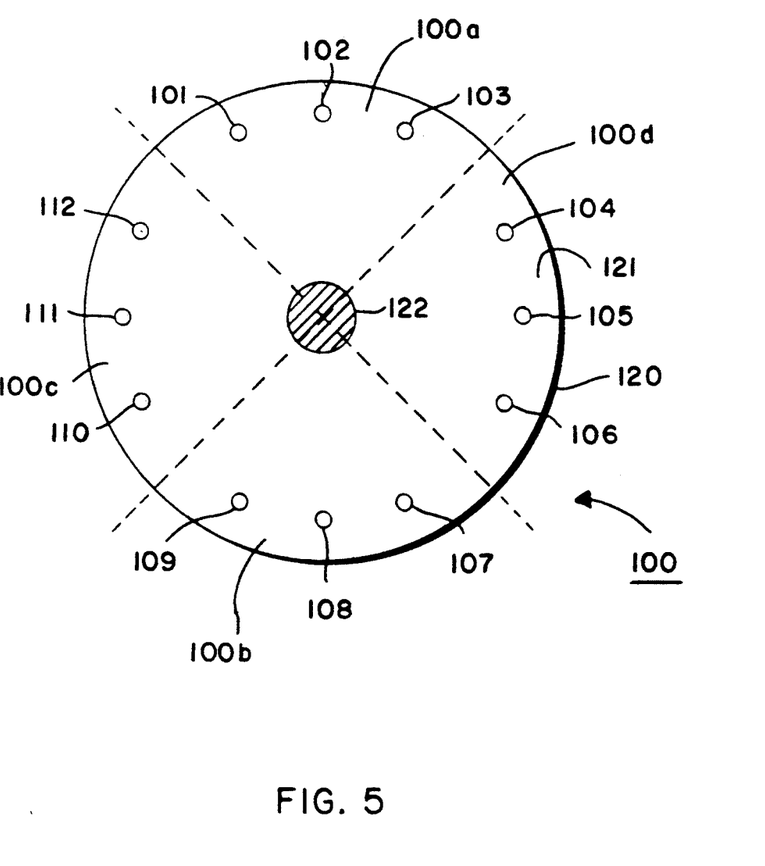
FIG. 5 is a cross sectional view of a position sensor used with the system of FIG. 1.

Now with reference to FIG. 5, the position sensor 100 is further described. The position sensor 100, as previously stated is in the form of a miniature twelve position mercury switch. Such switches are well known in the art, and the basic construction and operation of the sensor 100 are only summarized here to facilitate an understanding of the present invention. Sensors of this type generally include an electrically conductive case 120, in the form of an inverted metallic can, positioned on a substantially planar dielectric mounting base, generally indicated by reference numeral 121.

A droplet of mercury, generally indicated reference numeral 122, is free to move inside the case 120. Twelve electrically conductive pins 101-112 are circulalry positioned, equal distant apart on the mounting base 121. The pins 101-112 protrude through the base 120 so that they may externally connect to the sense lines 41c of the MUX 41 of FIG. 4. Each of the pins 101-112 provide one side of on ON/OFF switch, and the case 120 provides the other side via line 40v.

The mercury droplet 122 is the means used to selectively connect the various pins 101-112 to the case 120 to indicate ON states. When the mercury droplet 122 is simultaneous touching the case 120 and any of the pins 101-112, electrical current can flow from the case 120 to the pins 101-112 to indicate an ON state, otherwise an OFF state is indicated.

When the mounting base 121 is essentially horizontal or level, the mercury droplet 122 is generally in the middle of the mounting base 121, as shown in FIG. 5, and all of the pins 101-112 of the sensor 100 are in an OFF state. However, if the sensor is tilted in any direction, the force of gravity causes the mercury droplet 122 to seek a lower position on the mounting base 121 and consequently one or more of the pins 101-112 will be shorted to the case 120 by the mercury droplet 122 to indicate an ON state.

As shown in FIG. 6a, for slight angle of tilt of the sensor 100, approximately in the range of about 5 to 15 degrees, only a single one of the pins 101-112, for example pin 108, will be in an ON state. That is, the particular pin 108, indicates the direction of tilt.

As shown in FIG. 6b, when the sensor 100 is tilted to a greater angle, for example, in the range of about 15-25 degrees, more of the mercury droplet 122 will flow towards the periphery of the case 120, and two of the pins 101-112, for example pins 107-108, will be in an ON state to indicate the direction of tilt.

FIG. 6c shows the sensor 100 tilted to an even greater angle, for example the tilt being an angle greater than about 25 degrees, all of the mercury droplet 122 will be pooled along the periphery of the case 120, and as many as three of the pins 101-112, for example pins 107-109, will be in an ON state. Obviously, variations in the manufacture of the sensor 100 or the volume of the mercury droplet 122 may give different results.

It should now be apparent that the sensor 100 can be used to indicate the direction of tilt, as well as, the relative severity or angle of tilt of the sensor 100. In other words, the circular position of the pins 101-112 which are in an ON state give the general direction of tilt, and the number of the pins 101-112 that are ON give the relative angle of tilt of the sensor 100. Note that at any one time either 0, 1, 2, or 3 pins in an ON state, and that such pins are always adjacent.

Although the sensor 12 is capable of sensing twelve different directions of tilt, one direction for each of the pins 101-112, for the purpose of the invention, and as shown in FIG. 5, the pins 101-112 of the sensor 100 are arbitrarily grouped into four groups 100a-100d of three pins each, corresponding to the quadrants 5a-5d, respectively, as shown in FIG. 2. That is, the pins 101-103 in quadrant 100a correspond to the FORWARD head position (5a), pins 107-109 (100b) to the BACKWARD head position (5b), the pins 110-112 (100c) to LEFT head position (5c), and the pins 104-106 (100d) to RIGHT head position (5d). In other words, if any of the pins 101-112 in the various quadrants 100a-100d are in an ON state, the ON states of the pins 101-112 can be used to determine the direction of tilt of the head of the tennis player. The number of the pins 101-112 that are on in one the quadrants 100a-100d of the sensor 100 indicate the relative angle of tilt.

At this point it is probably appreciated that when the position processor 2 is mounted on the head of an active tennis player vigorously chasing an elusive tennis ball, the mercury droplet 122 of the sensor 100 is likely to bounce around inside the case 120 in a seemingly random and sporadic fashion. Therefore, merely sampling the ON/OFF states of the pins 101-112, in and of itself, is not disposed to give accurate positional information about the position of the head of the tennis player.

Therefore, to make sense out of this disorder, a software program is provide to sample, process, filter, the sampled ON/OFF states of the switches 101-112 of the sensor, and to display the thus processed ON/OFF states as positional information to the user. Furthermore, the software permits the user to selectively control the sensitive of the position processor 2, and to select the manner in which positional information is presented by setting the switches of the angel/sensitivit selector (ASEL) 42 and the quadrant selector (QSEL) 44 appropriately.

The software includes a polling procedure for sampling and processing ON/OFF states collected from the switches 42s, 44s, and 101-112, and an interrupt procedure to convey the processed ON/OFF states of the switches to the user.

FIG. 7 shows the steps of the polling procedure 50. The polling procedure will be described also with reference to FIG. 8 which shows the registers maintained by the polling procedure 50.

The registers of FIG. 7 include a sampling register (SAM-REG) 150 having twelve bits 151-162, each bit corresponding to one of the switches 101-112 of the sensor 100, respectively. A logical "0" in a bit indicating on OFF state, and a logical "1" indicating an ON state of any one of the switches 101-112.

Figure 8:
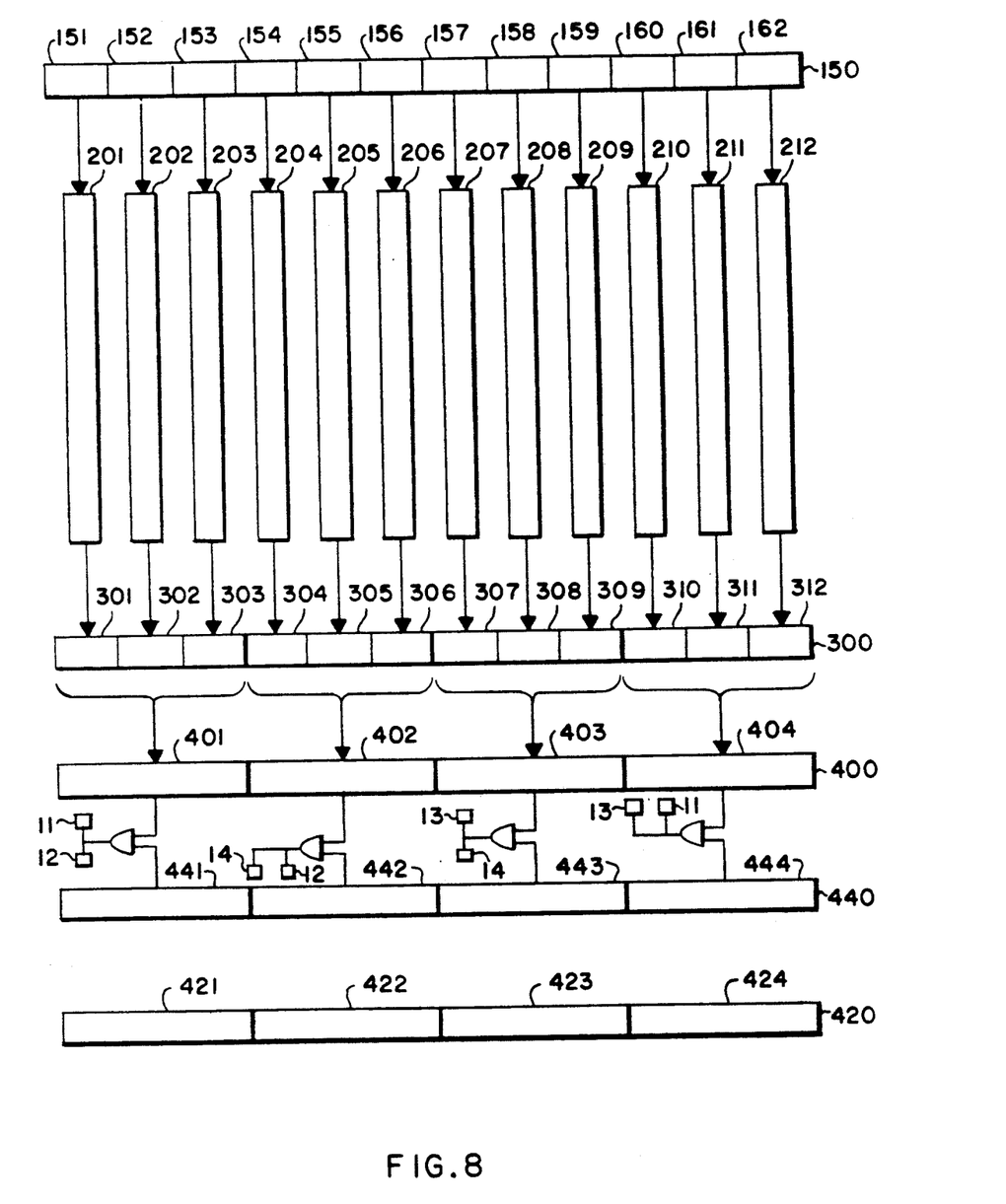
FIG. 8 illustrates the registers maintained by the polling procedure of FIG. 7.

There are twelve raw count registers (CNTREG) 201-212, one register for each of the bits 151-162 of the SAMREG 150, respectively. Each of the CNTREGs 201-212 can store a value in the range of 0 to 255.

A processed count register (PRCREG) 300 having twelve bits 301-312, one for each of the CNTREGs 201-212 respectively. And, a quadrant register (QUADREG) 400 including four bits 401-404, corresponding to groups of three bits of the PRCREG 300. That is, bits 301-303 representing a FORWARD (5a) position, bits 304-306 representing a RIGHT (5d) position, bits 307-309 representing a BACKWARD (5b) position, and bits 310-312 representing a LEFT (5c) position. Similarly, the bits 401-404 of the QUADREG also represent the four possible positions of the head.

Also included as registers are an angle and sensitivity selector register (ASREG) 420 having four bits 421-424, and a quadrant selector register (QREG) 440 having four bits 441-444. Registers 420 and 440 are for storing the sampled ON/OFF states of the ASSEL 42 and the QSEL 44, respectively.

The QREG 440 is used as follows, each of the bits 441-444 represents the head position quadrants FOR-WARD (5a), RIGHT (5d), BACKWARD (5b), and LEFT (5c) of FIG. 2. Quadrant information as indicated in the bits 401-404 of the QUADREG 400 will only be displayed if the corresponding bit in QREG 440 is also set to a logical "1," otherwise the quadrant information in QUADREG 400 will not be displayed. Effectively, the bits 441-444 of the QREG 440 are used as a logical AND function. As an example, if bits 441 and 443 of the QREG 420 are set to a logical "1", e.g., the binary value of QREG 420 is "1010" (i.e. decimal 10), that is rotary switch 42s is set to position position "10", positional information will only be conveyed to the user if the head is tilted either FORWARD or BACKWARD.

The bits 421-424 of the ASREG 420 are used to select predetermined combinations of angle settings and sensitivity with the ASSEL 44 as summarized in Table 1 below. The angle of tilt of the sensor 100 determined by an arbitrary angle setting, in the range of 1 to 3, the angle settings corresponding to the number of the pins 101-112 that are in an ON state. The sensitivity determined by the rate at which the sensor 100 is sampled. Sampling the various switches 100, 42s, and 44s at a higher rate making the system more sensitive, or more quickly responsive to changes in positions of the head. Sampling the switches at a lower rate makes the system less sensitive to changes in position. The rate is determined by multiplying a predetermined time delay, for example 0.4 ms by a predetermined sampling rate selected from values 5, 25, 50, 75, 100, 150, 170, or 250. The delay period being a period of time between sucessive sampling of the sensor 100. A sampling rate of 5 corresponding to the sensor 100 being sampled approximately every 2 ms, and a sampling rate of 25 causing the sensor to be sampled every 50 ms, and so forth.

The particular combinations of sampling rate and angle were empirically determined by use of the training system with a variety of players of different skill level and relative body motion. It should be obvious to one skilled in the art, that many other combinations are also possible.

TABLE 1

| Switch Position | Logical States | Angle Setting | Sampling Rate |
| --- | --- | --- | --- |
| 0 | 0000 | 1 | 5 |
| 1 | 0001 | 2 | 5 |
| 2 | 0010 | 3 | 5 |
| 3 | 0011 | 1 | 25 |
| 4 | 0100 | 2 | 25 |
| 5 | 0101 | 1 | 75 |
| 6 | 0110 | 2 | 75 |
| 7 | 0111 | 3 | 50 |
| 8 | 1000 | 1 | 100 |
| 9 | 1001 | 2 | 100 |
| 10 | 1010 | 1 | 150 |
| 11 | 1011 | 3 | 75 |
| 12 | 1100 | 2 | 150 |
| 13 | 1101 | 3 | 100 |
| 14 | 1110 | 3 | 170 |
| 15 | 1111 | 3 | 250 |

All of the registers 150, 201-212, 300, 400, 420, and 440 are initialized to logical "0" when the position processor 2 is turned on.

Now also with reference to FIG. 7, in step 51 of the procedure 50, switches 42s and 44s are sampled as to their ON/OFF states. The resulting ON/OFF states are stored in ASREG 420 and QREG 440, respectively, as bit patterns consisting of logical "0"s and logical "1"s.

In step 52, the polling procedure 50 determines the appropriate polling rate as indicated by the contents of ASREG 420 and delays execution of the procedure 50 for that period of time to achieve the desired polling rate or sensitivity of the training system. At the expiration of the predetermined time delay period, step 53 is executed.

Step 53 is used to sample the ON/OFF states of the switches 101-112 of the sensor 100. The switches 101-112 are sampled by the instructions of the step 52 selecting the switches 101-112 in turn via the MUX 41. The ON/OFF state of each of the switches 101-112 are stored in the bits 151-162 of the SAMREG 150, a logical "0" or "1" indicating, respectively, either on OFF or ON state of the corresponding switch 101-112 of the sensor 100 during a polling cycle. A polling cycle being one loop through the steps of the polling procedure 50.

Step 54 is used to maintain the raw counts of CNTREGs 201-212. The CNTREGs 201-212 are essentially used to indicate how long (or short) each of the switches 101-112 have been either ON or OFF. That is, in step 54, each of values stored in the CNTREGs 201-212 is incremented if the corresponding bit 151-162 of SAMREG 150 is a logical "1," otherwise the value is decremented. Note that the values stored in CNTREG 201-212 are not incremented over 255, nor decremented below 0. In other words, a high count in one of the registers 201-212 is indicative that a particular one of the switches 101-112 is more ON than OFF, a low count indicating the opposite. Or stated otherwise, a high count indicates that the head of the tennis player tends to be tilted in the direction of the pins 101-112 with the highest count.

In step 55, the counts stored in the CNTREG 201-212 are processed to give a general indication if one of the switches 101-112 is more ON than OFF. The counts are processed as follows. If one of the CNTREGs 201-212 stores a count greater than a HIGH threshold, the corresponding switch 101-112 is deemed to be mostly ON, and therefore, the corresponding bit 301-312 in the PRCREG 300 is set to a logical "1". If the count in one the CNTREGSs 201-212 is less than a LOW threshold the corresponding one of the bits 301-312 of the PRCREG is set to logical "0" to indicate that the corresponding switch 101-112 was mostly OFF. If the count is between the LOW and HIGH threshold, the corresponding bit 301-312 of the PRCREG 300 is not changed. The LOW and HIGH thresholds are spaced apart to provide sufficient hysterisis to filter out sporadic changes of ON and OFF states of the switches 101-112 induced by the spurious movement of the mercury droplet 122 inside the sensor 100 as the user moves about. The HIGH and LOW thresholds, in the preferred embodiment, as emperically determined to give good results, are set to counts of 192 and 64, respectively.

In step 56, the processed raw counts are further evaluated as follows. If one, two, or three adjacent bits in any one group of three bits 301-303, 304-306, 307-309, and 310-312 of the PRCREG 300 are set to a logical "1" proceed to step 57. If two adjacent bits in any two adjacent groups of bits are set, shift the bits 301-312 right one position, with end around carry, and proceed with step 57. If two adjacent bits are set in one group and one bit is set in an adjacent group, clear the single bit and and set the third bit in the group already having two bits sets, proceed with step 57.

In step 57, the quadrant register QUADREG 400 is set to the quadrant positions, FORWARD (5a), BACKWARD (5b), LEFT 5c, and RIGHT (5d) by setting the corresponding bits 401,403,402 and 404 of QUADREG 400 as follows. One of the bits 401-404 in QUADREG 400 is set to a logical "1" if any of the bits of the corresponding groups of bits are set in PRCREG to a logical "1" as evaluated in step 56. Otherwise, set the corresponding bit to logical "0".

In step 58, determine the angle of tilt of the sensor 100. If the angle setting is 3, all of the bits in a quadrant group of three in the PRCREG 300 must be set to logical "1" to indicate that the sensor 100 is tilted to a greatest angle. Otherwise set the corresponding bit in QUADREG 400 to logical "0". If the angle setting is 2, at least two bits in a quadrant group must be logical "1" in PRCREG 300, otherwise clear the corresponding bit in QUADREG 400. And, if the angle setting is 1, any one bit of a group of quadrant bits being logical "1" is sufficient to indicate that the sensor 100 is tilted at least a minimal angle.

After the completion of step 58 of polling procedure 50, execution proceeds in a repetitive and circular fashion with step 51. The function of the polling procedure is therefore, to sample the ON/OFF states of the switches at a predetermined sampling rate, the sampling rate determining the sensitivity of the training system. In addition, the procedure 50 evaluates and processes the sampled ON/OFF states to reduce states to postional information, including the direction and angle of tilt of the head of the user.

FIG. 9 shows the steps of the interrupt procedure 60 of the software of the position processor 2. In step 61, the LEDS 11-15 are turned ON or OFF depending on the bits 401-404 of the QUADREG 400 as processed by the steps 51-58 of the polling procedure 50. That is LEDS 11 and 12 are turned ON if bit 401 is logical "1", LEDS 13 and 14 are turned ON if bit 403 is logical "1", LEDS 11 and 13 are turned on if bit 404 is logical "1", and LEDS 12 and 14 are turned ON if bit 402 is logical "1", otherwise, if the bits 401-404 are all logical "0", turn on LED 15.

Likewise in step 62, the corresponding audible signals are generated. In the preferred embodiment, the pulsed and unpulsed tones at 3000, 1500 Hz are generated by using the internal timers of the microprocessor 40 which are initialized to generate interrupts at appropriate frequencies. In addition, in step 63, a 60 second interrupt time-out is maintained, to determine if any changes of positions have occurred in the last 60 seconds. If no changes in positions have been detected, the instructions of step 63 place the microprocessor 40 in a low power sleep state in order to conserve power.

The invention has now been described with reference to a specific embodiment for training atheletes. Other embodiments, such as a body monitoring systems for use during therapeutic physical rehabilitation, or systems for monitoring the head positions of drivers, should also be apparent to those skilled in the art. It is therefore not intended that this invention be limited except as indicated by the claims appended.

We claim:

1. An apparatus, for indicating the position of a body part, comprising:

a sensor for sensing a direction and angle of tilt, said sensor including a plurality of ON/OFF switches, each switch, at any one time, having either an ON or an OFF state, said ON and OFF states responsive to tilting of said sensor;
means for mounting said sensor on the body part;
means for sampling said ON and OFF states of said switches;
means, responsive to said means for sampling, for counting said ON and OFF states of each of said switches;
means, responsive to said means for counting, for converting the counts of said ON and OFF states to a sensed direction and angle of tilt;
means, responsive to said means for converting, for signalling said sensed direction and angle of tilt.

2. The apparatus as in claim 1 wherein said sensor is a twelve position mercury switch.

3. The apparatus as in claim 1 wherein said means for sampling includes a multiplexer.

4. The apparatus as in claim 1 wherein said means for counting includes a microprocessor.

5. The apparatus as in claim 1 wherein said means for signalling includes a visual unit and an audio unit.

6. The apparatus as in claim 5 wherein said visual unit includes five light emitting diodes, and said audio unit includes a speaker.

7. An apparatus, for training an athelete, comprising;
means for sensing a plurality of directions of tilt;
means for mounting said means for sensing on a body part of the athelete;
means, responsive to said means for sensing, for converting said plurality of directions to four quadrants of direction, said four quadrants being FORWARD, BACKWARD, LEFT, and RIGHT;
means, responsive to said means for converting, for signalling said four quadrants of direction.

8. A method, for sensing the position of a body part, comprising the steps of:
sensing the direction of tilt of the body part by means of a sensor mounted on the body part, said sensor including a plurality of ON/OFF switches, each ON/OFF switch having either on an or OFF state;
sampling said sensor to determine the ON/OFF states of said ON/OFF switches;
counting said ON/OFF states of said ON/OFF switches for a predetermined period of time;
converting said counted ON/OFF states to a direction of tilt; and
signalling said direction of tilt to the athlete.

9. The method as in claim 8 wherein said step of counting includes the steps of setting, for each of said switches, a low threshold count and a high threshold count, and indicating that a predetermined switch is in an ON state if the count for said predetermined switch exceeds said high threshold, and indicating that said predetermined switch is in on OFF state if the count for said predetermined switch is below said low threshold.

* * * * *